United States Patent
Patangay et al.

(10) Patent No.: US 8,352,032 B2
(45) Date of Patent: Jan. 8, 2013

(54) MONITORING RIGHT VENTRICULAR HEMODYNAMIC FUNCTION DURING PACING OPTIMIZATION

(75) Inventors: Abhilash Patangay, Inver Grove Heights, MN (US); Barun Maskara, Blaine, MN (US); Jonathan Kwok, Denville, NJ (US); Jiang Ding, Shoreview, MN (US); Yinghong Yu, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 984 days.

(21) Appl. No.: 12/235,220

(22) Filed: Sep. 22, 2008

(65) Prior Publication Data

US 2009/0118783 A1 May 7, 2009

Related U.S. Application Data

(60) Provisional application No. 61/001,439, filed on Nov. 1, 2007.

(51) Int. Cl.
*A61N 1/00* (2006.01)
(52) U.S. Cl. .......................................... 607/23
(58) Field of Classification Search ................ 607/9, 11, 607/15, 17, 18, 23
See application file for complete search history.

(56) References Cited

U.S. PATENT DOCUMENTS

| | | | |
|---|---|---|---|
| 5,487,752 A | 1/1996 | Salo et al. | |
| 5,626,623 A * | 5/1997 | Kieval et al. | 607/23 |
| 6,144,880 A | 11/2000 | Ding | |
| 6,285,907 B1 | 9/2001 | Kramer | |
| 7,184,835 B2 | 2/2007 | Kramer | |
| 7,890,172 B2 * | 2/2011 | Maskara et al. | 607/25 |
| 2003/0105496 A1 * | 6/2003 | Yu et al. | 607/17 |
| 2005/0027322 A1 | 2/2005 | Warkentin | |
| 2007/0060959 A1 | 3/2007 | Salo et al. | |
| 2007/0135705 A1 * | 6/2007 | Lorenz et al. | 600/410 |

* cited by examiner

*Primary Examiner* — Eric D. Bertram
*Assistant Examiner* — Roland Dinga
(74) *Attorney, Agent, or Firm* — Brooks, Cameron & Huebsch, PLLC

(57) ABSTRACT

Method and systems related to monitoring right ventricular function during pacing by a cardiac rhythm management device are described. One or more pacing parameters are selected to provide cardiac resynchronization therapy. For example, the one or more pacing parameters may be selected to provide an optimal or improved therapy. The heart is paced using the selected pacing parameters. While pacing with the selected parameters, pressure is sensed via a pressure sensor disposed the pulmonary artery. The sensed pressure is analyzed to determine right ventricular function achieved during the pacing using the selected pacing parameters. A signal, such as an alert signal or control signal, is generated based on the right ventricular function achieved during the pacing.

17 Claims, 9 Drawing Sheets

MONITORING RIGHT VENTRICULAR HEMODYNAMIC FUNCTION DURING PACING OPTIMIZATION

RELATED APPLICATIONS

This application claims the benefit of Provisional Patent Application Ser. No. 61/001,439 filed on Nov. 1, 2007, to which priority is claimed pursuant to 35 U.S.C. §119(e) and which is hereby incorporated herein by reference in its entirety.

FIELD OF THE INVENTION

The present invention relates generally to cardiac pacing therapy, and more specifically, to methods and systems for optimizing pacing parameters for cardiac resynchronization therapy while monitoring right ventricular hemodynamic function.

BACKGROUND OF THE INVENTION

Cardiac rhythm management devices have been developed that provide pacing stimulation to one or more heart chambers in an attempt to improve the rhythm and coordination of atrial and/or ventricular contractions. Cardiac rhythm management devices typically include circuitry to sense signals from the heart and a pulse generator for providing electrical stimulation to the heart. Leads extending into the patient's heart chambers and/or into veins of the heart are coupled to electrodes that sense the heart's electrical signals and for delivering stimulation to the heart in accordance with various therapies for treating cardiac arrhythmias.

Pacemakers are cardiac rhythm management devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

Pacing therapy has been used in the treatment of various types of heart failure (HF). Generally, HF is associated with diminished pumping power of the heart, resulting in the inability to deliver enough blood to meet the demands of peripheral tissues. HF may cause weakness, loss of breath, and build up of fluids in the lungs and other body tissues. HF may affect the left heart, right heart or both sides of the heart. HF may occur when deterioration of the muscles of the heart produce an enlargement of the heart and/or reduced contractility. The reduced contractility decreases the cardiac output of blood and may result in an increased heart rate. In some cases, HF is caused by unsynchronized contractions of the left and right heart chambers, such as atrial or ventricular dysynchrony. When the left or right ventricles are affected, unsynchronized contractions can significantly decrease the pumping efficiency of the heart.

Pacing therapy can promote synchronization of heart chamber contractions and/or increase contractility of the cardiac tissue to improve cardiac function. Therapy that promotes cardiac synchronization is generally referred to as cardiac resynchronization therapy (CRT). Some cardiac devices are capable of delivering CRT by pacing multiple heart chambers. Pacing pulses are delivered to the heart chambers in a sequence that causes the heart chambers to contract in synchrony, increasing the pumping power of the heart and delivering more blood to the peripheral tissues of the body. In the case of dysynchrony of right and left ventricular contractions, a biventricular pacing therapy may pace one or both ventricles. Bi-atrial pacing or pacing of all four heart chambers may alternatively be used.

Some patients, in particular those suffering from HF, benefit from pacing pulses applied at multiple electrodes disposed within or about a heart chamber. The sequence of the pacing pulses applied to the multiple electrodes may be designed to increase contractility and/or synchrony of the contractions.

Pacing therapy has been proven valuable in treating physiological effects associated with decreased cardiac function. Selecting pacing parameters that provide optimal pacing therapy for HF and/or other cardiac rhythm disorders is desirable. The present invention fulfills these and other needs, and offers advantages over prior art approaches.

SUMMARY OF THE INVENTION

Embodiments of the present invention are related to methods and systems for determining pacing parameters for cardiac resynchronization therapy while monitoring right ventricular hemodynamic function.

One embodiment involves a method of operating a cardiac rhythm management device. One or more pacing parameters are selected to provide cardiac resynchronization therapy. For example, the one or more pacing parameters may be selected to provide an optimal therapy. The heart is paced using the selected pacing parameters. While pacing with the selected parameters, pressure is sensed using a pressure sensor disposed the patient's pulmonary artery. The sensed pressure is analyzed to determine right ventricular function achieved while the heart is paced using the selected pacing parameters. A signal is generated, such as an alert signal and/or control signal, based on the right ventricular function achieved during the pacing.

Another embodiment of the invention is directed to a cardiac rhythm management system. The system includes a cardiac resynchronization optimization module configured to determine pacing parameters for cardiac resynchronization therapy (CRT). A pacing therapy circuitry is configured to deliver pacing using the CRT pacing parameters. While pacing, a pulmonary artery pressure sensor disposed in the pulmonary artery senses the pulmonary artery pressure. A right ventricular function analysis module analyzes the sensed pulmonary artery pressure to determine right ventricular function achieved during the pacing. A controller is configured to generate a signal based on the right ventricular function achieved during the pacing. For example, the controller may generate an alert signal or may generate a control signal to override the pacing parameters if degradation of the right ventricular function is detected.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
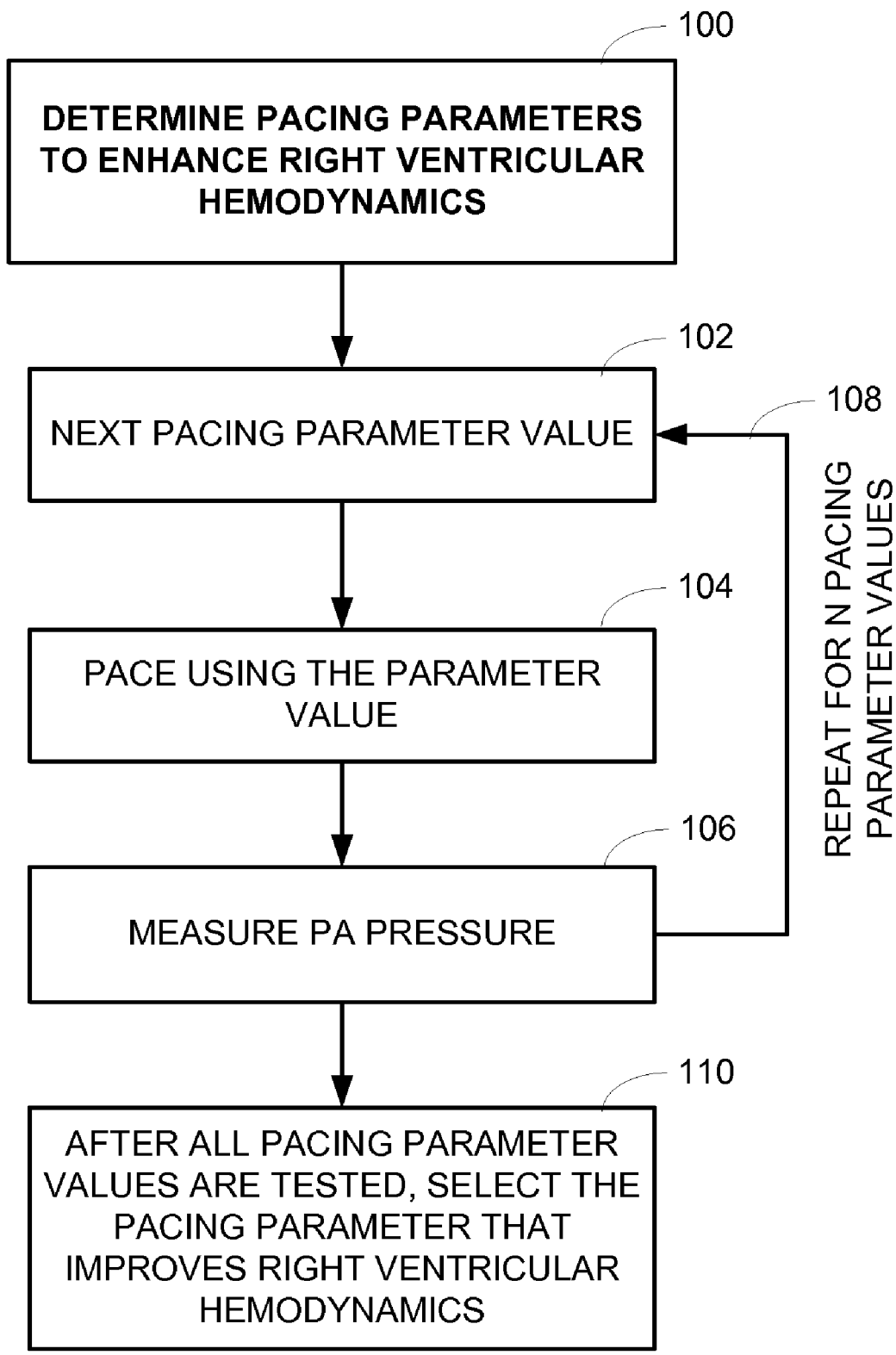
FIG. 1 is a flow diagram illustrating a process for determining a pacing parameter value that provides improved right ventricular (RV) hemodynamic function in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

Embodiments of the invention involve the use of pressure measurements acquired from a sensor disposed in the pulmonary artery (PA), or parameters derived from the sensed PA pressure signal, to determine pacing parameters that provide optimal right ventricular (RV) hemodynamics. The measured or derived PA pressure parameters may include, for example, PA end diastolic pressure (PAEDP), PA end systolic pressure (PAESP), PA pulse pressure (PAPP), RV $dp/dt_{max}$, RV $dp/dt_{min}$, PAEDP timing and/or other PA pressure parameters that are indicative of RV hemodynamic function.

According to some embodiments, the system implements a pacing optimization protocol that cycles through several of values of a pacing parameter or combinations of pacing parameters to improve or optimize cardiac function. Such an optimization protocol may be performed, for example, to determine pacing parameters that improve or produce optimal RV hemodynamic function. The pacing optimization protocol involves cycling through any combination of pacing timing delays, pacing sites, pacing modes, pacing sequences, or other parameters that involve the application of electrical impulses to cardiac tissue. For each of the pacing parameter values or combination of values tested, PA pressure is sensed and the sensed PA pressure signal is analyzed with respect to RV hemodynamic function. The pacing parameter value that provides improved or optimal RV hemodynamic function may be selected for use in a subsequent pacing therapy.

Other embodiments involve the use of PA pressure sensing to monitor RV hemodynamic function in conjunction with a protocol that determines pacing parameters to improve or optimize LV hemodynamic function. For example, cardiac resynchronization therapy optimization (CRTO) may optimize pacing parameters for LV hemodynamics. In some embodiments, during the CRTO, or other protocol or process that determines pacing parameters for improved LV hemodynamics, the patient's RV hemodynamic function is monitored by sensing PA pressure. If the pacing parameters that are optimal for CRT cause unacceptable degradation of RV function, an alert may be generated or other action may be taken.

The efficiency of the heart's pumping action depends on the timing of atrial and ventricular contractions and the pressure gradients between the heart's chambers. The superior vena cava and inferior vena cava return blood from the body to the right atrium. The blood from the right atrium flows through the tricuspid valve and into the right ventricle. The blood is pumped by the right ventricle through the pulmonary valve to the lungs via the right and left pulmonary arteries. Oxygenated blood from the lungs reenters the heart through the left atrium and passes through the mitral valve into the left ventricle. The blood is pumped by the left ventricle into the aorta via the aortic valve.

Mitral value closure and diastolic filling are influenced by the timing of atrial and ventricular contraction. If the AV interval is too long, mitral valve closure may occur early and reduce diastolic filling time. If the AV interval is too short, atrial contribution to ventricular filling is impaired because the mitral valve fails to close before left ventricular systole.

The effectiveness of the pumping action of the RV can be correlated to PA pressure. Embodiments of the invention use direct PA pressure sensing or parameters derived from the PA pressure signal to determine RV function for several values of a pacing parameter, such as the AV delay. The pacing parameter value that provides optimal RV hemodynamic function can be determined 100 using the protocol illustrated in the flow diagram of FIG. 1. Several values of the pacing parameter can be tested. While pacing with the parameter value that is being tested, the PA pressure is sensed using a PA pressure sensor disposed in the pulmonary artery.

As illustrated in FIG. 1, the protocol tests pacing parameter values by iteratively pacing 102, 104 using each of N parameter values. The PA pressure is measured 106 during each iterative loop. The protocol repeats 108 the procedure of steps 102-106 to scan through all N values of the pacing parameter. After all the pacing parameter values are tested, the value that improves or provides optimal RV hemodynamics is selected 110. The selected pacing parameter value is used for a subsequent pacing therapy.

Figure 2:
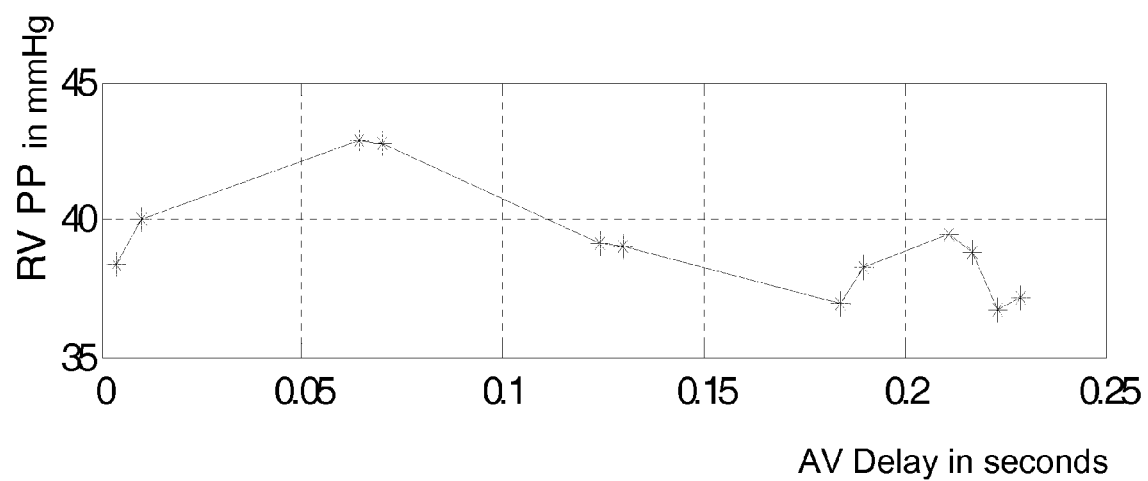
FIG. 2 is a plot of data illustrating atrioventricular (AV) delay optimization based on RV pulse pressure in accordance with embodiments of the present invention.

The graph of FIG. 2 illustrates implementation of the above process for selection of AV delay to achieve optimal RV hemodynamic function. The process of FIG. 1 is used to scan through twelve AV delay values ranging between 10 and 230 ms. Pacing is delivered using each of the AV delay values while sensing PA pressure. The sensed PA pressure signal is used to derive RV pulse pressure (RVPP) which is indicative of RV hemodynamic function. In this example, the RVPP corresponding to optimal RV function is the maximum pulse pressure which occurs at an AV delay value of about 70 ms.

Figure 3:
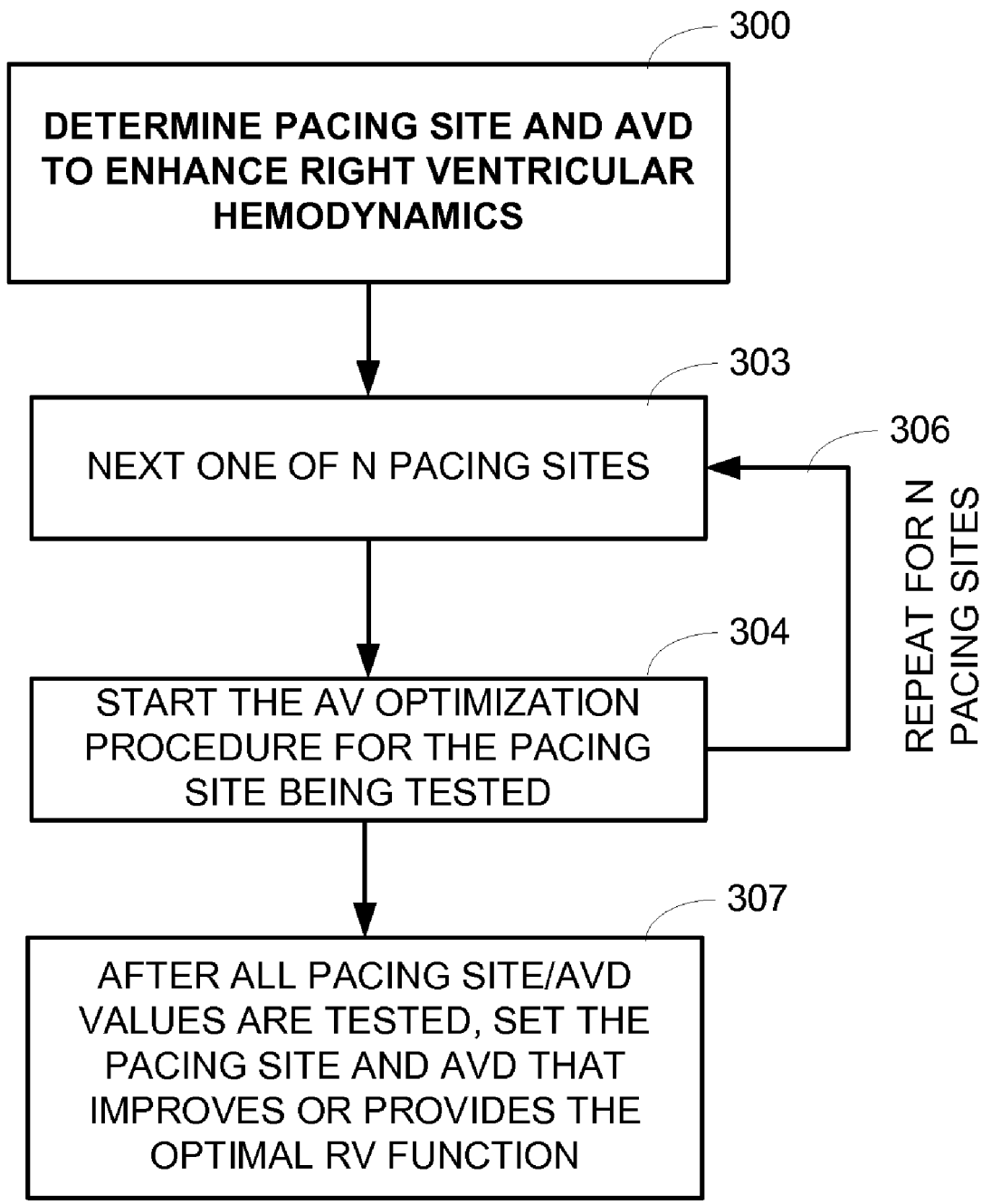
FIG. 3 is a flow diagram illustrating pacing site and AV delay selection for RV hemodynamic function based on sensed pulmonary artery (PA) pressure according to embodiments of the invention.

The pacing parameters that affect RV function are often interrelated. Multiple pacing parameters may be optimized, for example, through the use of several iterative sub-processes. Some configurations involve cardiac rhythm management (CRM) systems having multiple pacing electrodes providing the capability to pace multiple sites in, on, or about a heart chamber. Pacing with a particular AV delay value may provide optimal RV function for a first pacing site, but pacing with the same AV delay value may be sub-optimal at a second pacing site. As illustrated in FIG. 3, in implementations where it is desirable to select both AV delay and pacing site, the test protocol may scan through all AV delay values for each of several pacing site locations. PA pressure is sensed for each combination of AV delay value and pacing site. The combination that provides improved or optimal RV hemodynamic function is selected for use in pacing therapy.

The flow diagram of FIG. 3 illustrates a process for selecting multiple interrelated pacing parameters (e.g., pacing site and AV delay) that enhance or optimize 300 RV hemodynamic function. Each pacing site is tested 302 by scanning through all available AV delay values. Scanning through the AV delay values may be achieved using a subprocess that optimizes AV delay as illustrated in the flow diagram of FIG. 3. The PA pressure is sensed for each combination of pacing site and AV delay value. The process continues until every combination of N pacing sites and AV delay values has been tested. The PA pressures for each combination are analyzed to determine 307 the pacing site and AV delay that improves or provides the optimal RV hemodynamic function.

Commonly, HF patients have high blood pressure, either as a cause or effect of heart conditions. Treating HF patients often involves therapy to lower blood pressure over the long term. However, by acutely maximizing PA pressure or parameters derived from measured PA pressure (i.e., doing so over a short period of time), the cardiac output can be momentarily and periodically increased to improve heart condition, for example, by inducing reverse remodeling. Generally, acute therapies rely on the heart's short-term reaction to some variation of a therapy parameter before the body's baroreflex response can adjust to the variation.

According to some embodiments of the invention, a pacing parameter (e.g., pacing timing interval, pacing site and/or other pacing parameter) is varied during multiple repetitions of an acute burst pacing protocol. The parameter value is different for each of the bursts, and the resulting changes to PA pressure are observed. PA pressures that occur in time periods between the bursts may also be observed in order to determine a baseline reading. Assuming that one of the pacing parameter values results in optimal or improved hemodynamics, the parameter value may be used as part of a therapy for increasing heart function.

Figure 4:
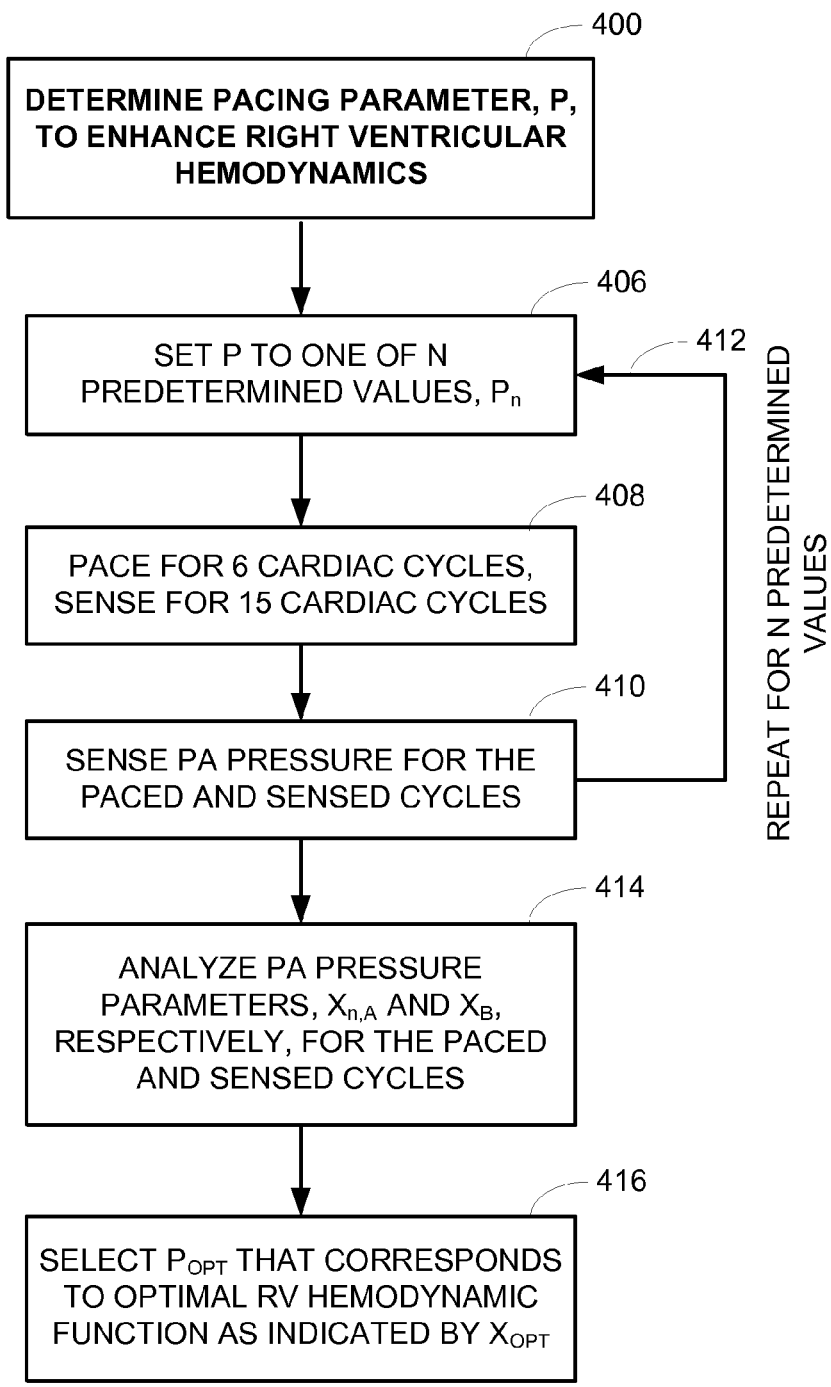
FIG. 4 is a flow diagram that illustrates the use of an acute pacing protocol in a procedure for optimizing ventricular hemodynamics based on sensed PA pressure according to embodiments of the invention.

Turning now to FIG. 4, there is shown a flow diagram that illustrates a procedure 400 for optimizing ventricular hemodynamics based on sensed PA pressure according to an embodiment of the invention. The procedure involves pacing 402 using N different values of a pacing parameter P. The parameter P may be any value that affects the application of electrical impulses to cardiac tissue. Typical examples of P include AV delay, VV delay, pacing site, pacing sequence, etc. The variable P may be continuous or discrete, and the acceptable range of P may be patient-specific.

The procedure 400 involves entering a loop 406-410 that is repeated N times, once for each value of $P_n$, where n is an integer from 1-N. For each repetition, n, of the loop 406-410, the value of pacing parameter, P, is set 406 to one of the pacing parameter values, the selected value being annotated as $P_n$. The value of $P_n$ is used to apply pacing 408 for A cardiac cycles, and a value, $X_{n,A}$, is analyzed 414 from the PA pressure signal sensed during the A paced cardiac cycles. $X_{n,A}$ may be a PA parameter that is acquired directly from the PA pressure signal sensed during the A paced cycles or derived using the sensed PA pressure signal. The number of paced cardiac cycles, represented by A, is chosen to substantially affect measured PA pressure without allowing time for the baroreflex function to adjust for the change in pressure. After the A pacing cycles are applied 408, an intervening period of sensing 408 the PA pressure with no pacing or pacing with predetermined values is performed for B cardiac cycles. Typically, the value of B will be significantly larger than A.

The same PA parameter that is analyzed 414 from PA sensing during the pacing phase is also analyzed 414 for the sensing phase 408. These latter measurements are represented as $X_B$. The sensing phase may involve no pacing at all, or pacing using pre-established values that mimic the intrinsic response of a particular patient. After the sensing phase 408 for a particular repetition, the value of n is incremented 412 and the loop 406-410 repeats for another repetition.

After N repetitions are complete, a baseline value of PA pressure ($X_{BASE}$) may be determined using the measurements taken during one or all of the sensed cycles. An optimal value (e.g., maximum PA diastolic (PAD) pressure, maximum RVPP, etc.) of a parameter measured or derived from the PA pressure signal, X, ($X_{OPT}$), is identified from the PA pressure signal sensed in pacing periods. $X_{OPT}$ may rely on the baseline measured value $X_{BASE}$. $X_{BASE}$ can be used as a reference for analyzing $X_{n,A}$ for the paced cycles. The use of a reference in the analysis of $X_{n,A}$ reduces the effect of compensation by baroreflex response during the acute protocol.

An actual or estimated optimal value of the pacing P ($P_{OPT}$) that corresponds to $X_{OPT}$ is selected 416 to deliver a pacing therapy. The procedure 400 may be used to select any pacing parameter P known in the art. One useful application involves using AV delay as the parameter P.

Figure 5:
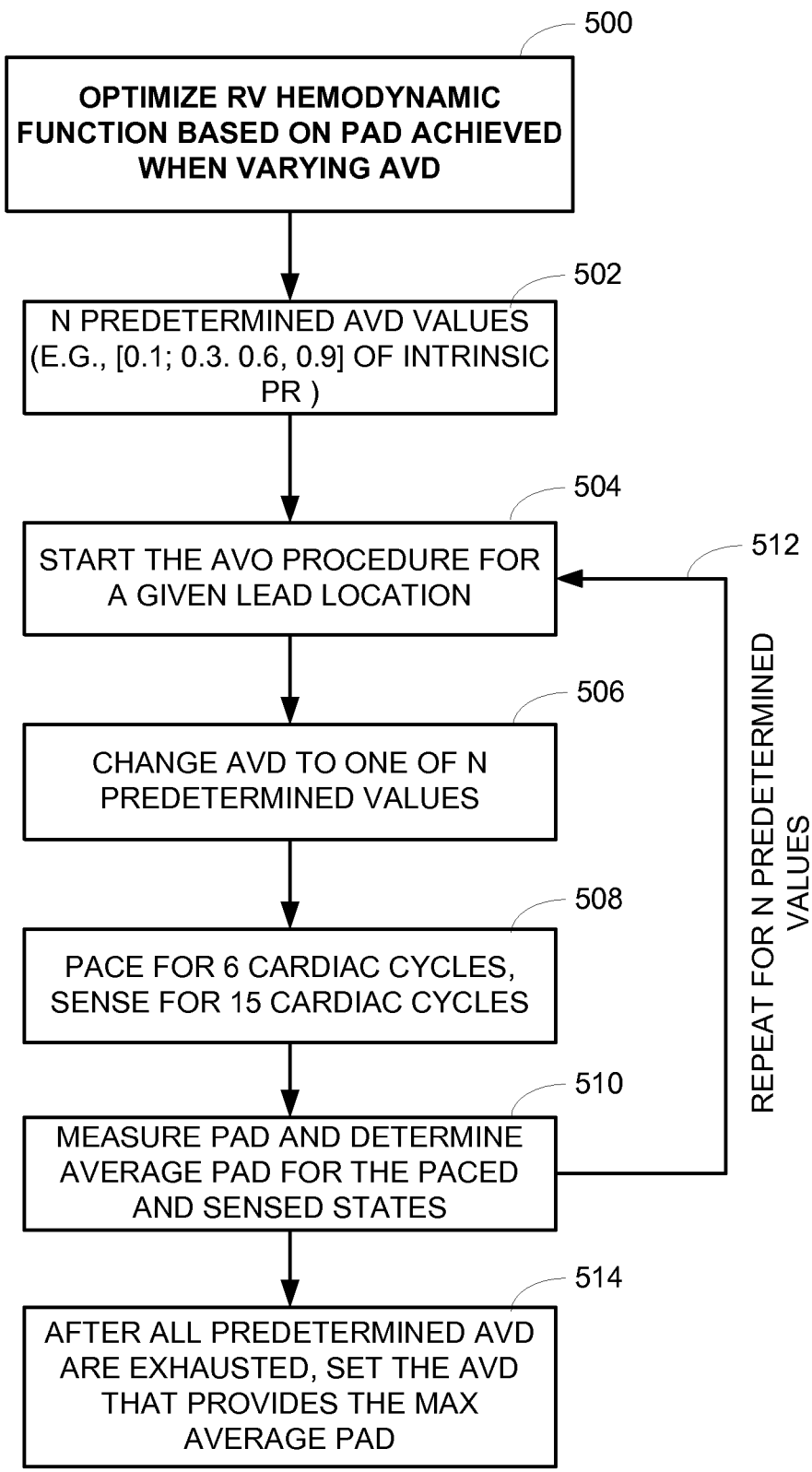
FIG. 5 is a flow diagram that illustrates the use of an acute pacing protocol in a procedure for optimizing AV delay and pacing site for optimal RV hemodynamic function based on sensed PA pressure according to embodiments of the invention.

In reference now to FIG. 5, there is shown a flow chart that illustrates a procedure 500 for optimizing RV hemodynamics based on PA diastolic (PAD) pressure determined from sensed PA pressure while varying AV delay (AVD) according to an embodiment of the invention. The procedure 500 involves using 502 N predetermined AVD values. For example, the values may be 10%, 30%, 60% and 90% of a patient's intrinsic PR timing. An AV optimization (AVO) procedure is started 504 for a given pacing site. The AVD is changed 506 to one of the N predetermined AVD values, and A pacing cycles and B sensing cycles are performed 508. In this example, the AVO procedure 504-510 involves pacing for six cardiac cycles and sensing for 15 cardiac cycles. The pacing and sensing cycles may be repeated multiple times for the AV delay. The paced PA pressure is sensed and the measured PAD and average PAD is determined 510 for the respective paced and sensed cycles from the sensed PA pressure. The average PAD for the sensed cycles is used as the baseline PAD. The subprocess 504-510 is repeated 512 for the N predetermined AVD values. After all the predetermined AVD values are exhausted, the AVD is set 514 to the value that produces the maximum average paced PAD relative to the baseline sensed PAD.

Patients that suffer from heart failure may be implanted with cardiac rhythm management devices that provide pacing to resynchronize the contractions of right and left heart chambers. Cardiac resynchronization therapy (CRT) involves pacing delivered to one or multiple pacing sites in a left heart chamber, typically the left ventricle, and to one or multiple pacing sites in a contralateral right heart chamber (e.g., right ventricle). Pacing to the right and left ventricles and/or right and left atria may be performed in addition to atrioventricular pacing typically used to treat bradyarrythmia.

In CRT that involves right and left ventricular pacing, the ventricles are typically paced with a timed delay between the right and left ventricular paces of each cardiac cycle. The delay between right and left ventricular paces is referred to as the interventricular delay (IVD) or V-V delay.

CRT for left-sided heart failure may involve selecting pacing parameters, such as pacing site, pacing sequence, AV delay, and/or IVD, that provide optimal or improved LV hemodynamic function. However, pacing to achieve improved or optimal LV function may degrade or provide sub-optimal RV hemodynamic function. Some embodiments involve monitoring RV hemodynamic function using sensed PA pressure in conjunction with optimization of pacing parameters for CRT. If the optimal pacing parameters returned by a CRT optimization procedure cause a significant degradation of RV hemodynamic function an appropriate response is initiated. Degraded or sub-optimal RV hemodynamic function may be detected, for example, by comparing the measured PA pressure, or a derivative value thereof, to a threshold value.

In suboptimal or degraded RV function is detected, a signal may be generated to alert the patient's physician or health care provider. In some configurations, alternate pacing parameter values may be automatically selected that are not optimized for either RV function or LV function alone, but provide improved overall cardiac function. Optimization of CRT pacing parameter values may be performed by a variety of techniques. After implant, for example, the pacing parameters may be adjusted for improved or optimal CRT using echocardiographic and/or electrophysiological studies. Adjustment of CRT pacing parameters may be performed based on sensed left ventricular hemodynamic parameters.

Commonly owned U.S. Pat. Nos. 6,144,880 and 7,184,835 describe multiple ways to determine parameters for ventricular pacing. Commonly owned U.S. Pat. Nos. 6,144,880 and 7,184,835, describe techniques for optimization of LV function that are based on certain intrinsic electrical or mechanical events that have a predictable timing relationship to the delivery of optimally timed ventricular pacing pulses. In other approaches, described in commonly owned U.S. Pat. No. 6,285,907, an optimal AV delay for bi-ventricular pacing is determined based on an underlying intrinsic heart rate, the AV interval, or sensor indicated rate. U.S. Pat. Nos. 6,144,880, 6,285,907, and 7,184,835 are incorporated herein by reference. Any method for determining CRT pacing parameters, including techniques described in the above-referenced patents, or other techniques, may be used in conjunction with monitoring RV hemodynamics using measured PA pressure as described herein.

Figure 6:
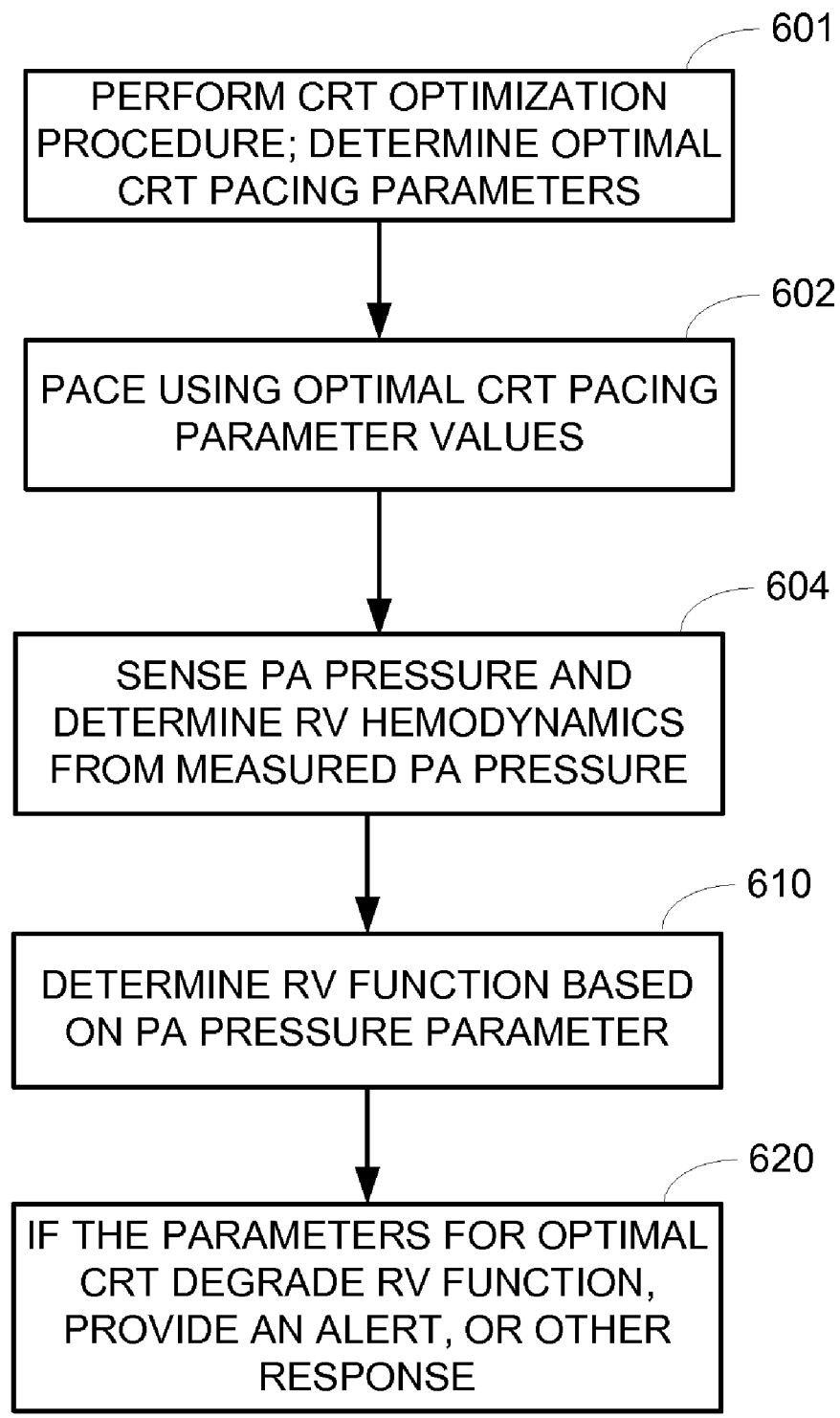
FIG. 6 is a flow diagram that illustrates a procedure for monitoring RV function in conjunction with CRT optimization in accordance with embodiments of the invention.

The flow chart of FIG. 6 illustrates an exemplary process for monitoring RV function in conjunction with optimization of CRT pacing parameters. CRT optimization (CRTO) procedure is performed 601 by any CRTO technique to determine the optimal pacing delays, pacing site(s), pacing sequence(s) and/or other pacing parameter values for CRT and/or to enhance LV function. The optimization of pacing parameters for CRT may be implemented shortly after implantation and/or may be implemented as a follow-up, ambulatory CRT optimization.

Pacing is delivered using 602 the parameters returned by the CRT optimization procedure as providing optimal CRT. During delivery of the pacing, the PA pressure is sensed 604. A parameter measured or derived from the sensed PA pressure signal is used to determine 610 RV hemodynamic function while pacing with the CRT pacing parameters returned by the CRTO procedure. The degradation of RV function may be determined, for example, by comparing the measured or derived PA pressure parameter to a threshold.

In some implementations, the RV function achieved during pacing with parameters optimized for CRT may be determined via an acute testing protocol as described more fully in connection with FIG. 5. Pacing is delivered using the optimal parameters for CRT during a first period of time (pacing phase) and no pacing or modified pacing may be delivered for a second period of time (sensing phase). The sensing phase may involve no pacing at all, or pacing using pre-established values that mimic the intrinsic response of a particular patient. During both pacing and sensing phases, the PA pressure signal is sensed. The PA pressure signal sensed during the sensing phase may be used to establish a baseline for the PA pressure. If the PA pressure signal sensed during the pacing phase decreases by a predetermined amount or is less than a threshold value, for example, then RV function may be degraded by pacing with the optimal CRT pacing parameters. In some embodiments, the pacing parameters may be automatically overridden if RV function degrades during the testing protocol.

If pacing using the optimal CRT parameters degrades 620 RV function, a responsive action is implemented. For example, an alert may be sent to the patient's physician via an advanced patient management (APM) or the alert may displayed on a device programmer or other hand-held, patient worn, or bedside device. When interacting with the APM system or device programmer, the physician may have the option to override the CRT pacing parameters recommended by the CRT optimization procedure to reduce the deterioration in RV function. In some configurations, the CRM or APM system may include the functionality to determine pacing parameters that are optimal when both RV and LV function are considered.

Figure 7A:
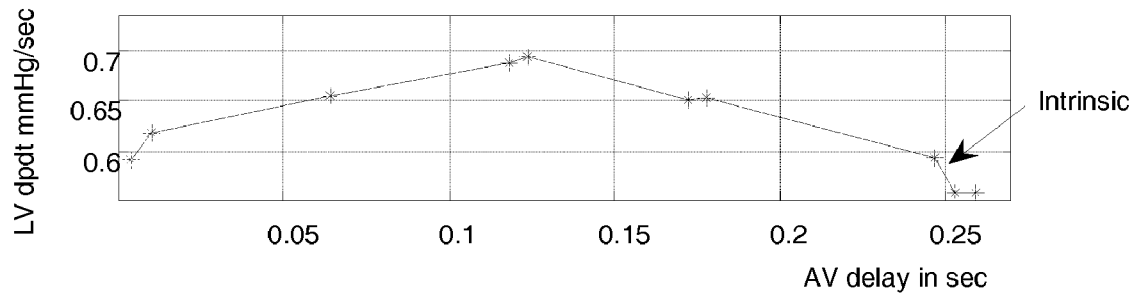
FIGS. 7A and 7B are graphs of LV dp/dt and RV pulse pressure, respectively, vs. AV delay.
Figure 7B:
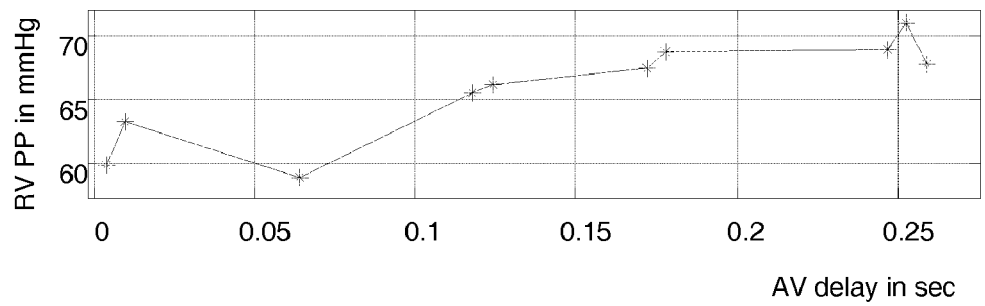

The graphs provided in FIGS. 7A and 7B illustrate the effect of pacing with various AV delays on LV and RV hemodynamic function. FIG. 7A illustrates the relationship between LV dp/dt, which is indicative of LV function, and AV delay. FIG. 7B illustrates the relationship between RV PP and AV delay. Comparison of FIGS. 7A and 7B illustrates that an AV delay providing optimal LV hemodynamic function does not necessarily provide optimal hemodynamic function for the RV. Thus, as recognized by the procedures described herein, it is desirable to monitor RV hemodynamics in conjunction with a procedure to determined optimal pacing parameters for LV function in order to maintain overall cardiac pumping effectiveness.

In some implementations, CRT may be optimized for particular patient conditions. For example, the CRT pacing parameters adjusted to provide optimal LV function for varying patient conditions, including sleep or wake conditions, activity levels, drug therapies, and/or postures (e.g., standing, sitting, prone) and/or other conditions/states. If the pacing parameters during any of the particular patient conditions cause a degradation of RV function, as determined via the sensed PA pressure, then the system may issue an alert or take other action.

CRT optimization may be performed in a clinical setting, where a patient's condition is actively monitored by a clinician. However, ambulatory CRT optimization is also possible, where various (typically mild) variations of a parameter are changed in use and under a number of different patient conditions (e.g., sleep, exercise, working) to either determine new parameter values or to optimize existing parameters. Any optimal parameters found during CRT optimization can be used in a regular regime of therapy, typically by application via implantable pacing system.

A methodology of the present invention may be implemented in a variety of medical diagnostic and/or therapeutic devices and systems, include implantable and patient-external devices and systems. For example, a methodology of the present invention may be implemented entirely by an implanted device (e.g., pacemaker, ICD, CRT devices), entirely by a patient-external system, or in a distributed manner by both implanted and patient-external devices or systems. In the context of a patient-external or distributed approach, various external systems may be employed, such as a programmer and/or a networked system, such as an advanced patient management system.

Figure 8:
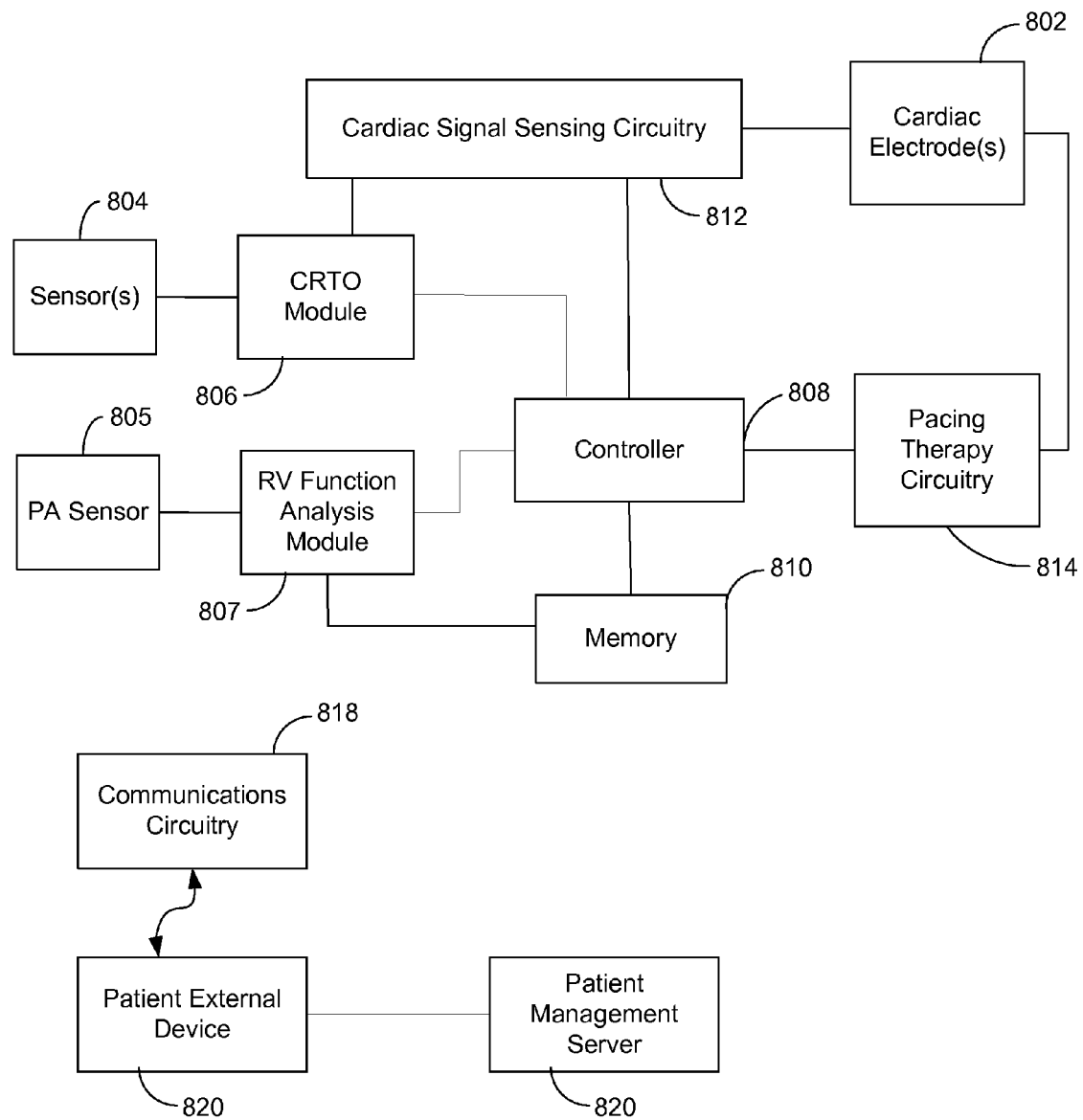
FIG. 8 is a block diagram of circuitry that may be used for implementing a methodology in accordance with embodiments of the present invention.

In reference now to FIG. 8, a block diagram shows system that implements a methodology that provides optimal pacing parameters for RV function and/or monitors RV function in conjunction with CRT optimization in accordance with embodiments of the invention. One or more cardiac electrodes 802 may be positioned or disposed at multiple locations within a heart chamber and/or vasculature. In the context of an electrode implantation procedure, a candidate pacing site may be evaluated/optimized using a lead that includes one or more electrodes. In the context of post-implant evaluations, one or more implanted pacing sites may be evaluated/optimized.

The system may include a module 806 that implements optimization of CRT pacing parameters. The CRT optimization may rely on information acquired from sensors 804 configured to sense physiological factors indicative of a patient's hemodynamic status. Useful sensors 804 include a sensor or sensors that detect heart sounds (e.g., microphone, accelerometer), a pressure sensor (e.g., left arterial pressure sensor or left ventricular pressure sensor), and/or an impedance sensor configured to measure cardiac stroke, among others. Signals produced by the one or more sensors 804 may be communicated to a CRTO module 806, which processes the sensor signals or other information to determine the optimal CRT parameters for pacing to improve LV function.

The CRTO module returns optimal pacing parameters to the controller 808. The controller 808 is coupled to the CRTO module 806, the RV Function Analysis module 807, memory 810, cardiac signal sensing circuitry 812, and pacing therapy circuitry 814. The memory 810 is configured to store program instructions and/or data. In addition, the stored information may be used to provide a log of events for display or analysis at a later time. The memory 810 may be configured to store program instructions for a CRT optimization algorithm or RV function analysis algorithm of a type described previously. Alternatively, the algorithms may be stored on a patient-external device or system.

The controller 808 executes program instructions to control the delivery of pacing therapy, to initiate CRTO algorithms, and/or to initiate RV function analysis via the RV function module 807. For example, after CRTO is performed by the CRTO module 806, the controller 808 may initiate and control delivery of pacing using the pacing parameters returned by the CRTO module 806. While pacing is delivered using the pacing parameters optimized for CRT or LV function enhancement, the RV function module 807 analyzes the sensed PA pressure for degradation of RV function. If the PA pressure indicates that RV function has degraded beyond a threshold amount, the RV function analysis module 807 provides an indication signal to the Controller 808. The Controller 808 may initiate an alert, may change the pacing parameters to default values, or may take other action.

The controller 808 is preferably coupled to communications circuitry 818 which allows the device to communicate with other devices 820, such as a patient-external programmer or advanced patient management system. In some implementations, an advanced patient management (APM) system may be used to collect CRT patient data for purposes of developing patient population data from which a CRT optimization algorithm may be developed.

Although not specifically shown in FIG. 8, the CRM system may also include an arrhythmia detection module configured to recognize tachyarrhythmias based on cardiac rate and/or cardiac signal morphology. The CRM system may also include a tachyarrhythmia therapy module configure to provide tachyarrhythmia therapies such as anti-tachyarrhythmia pacing (ATP), cardioversion, or defibrillation.

Figure 9:
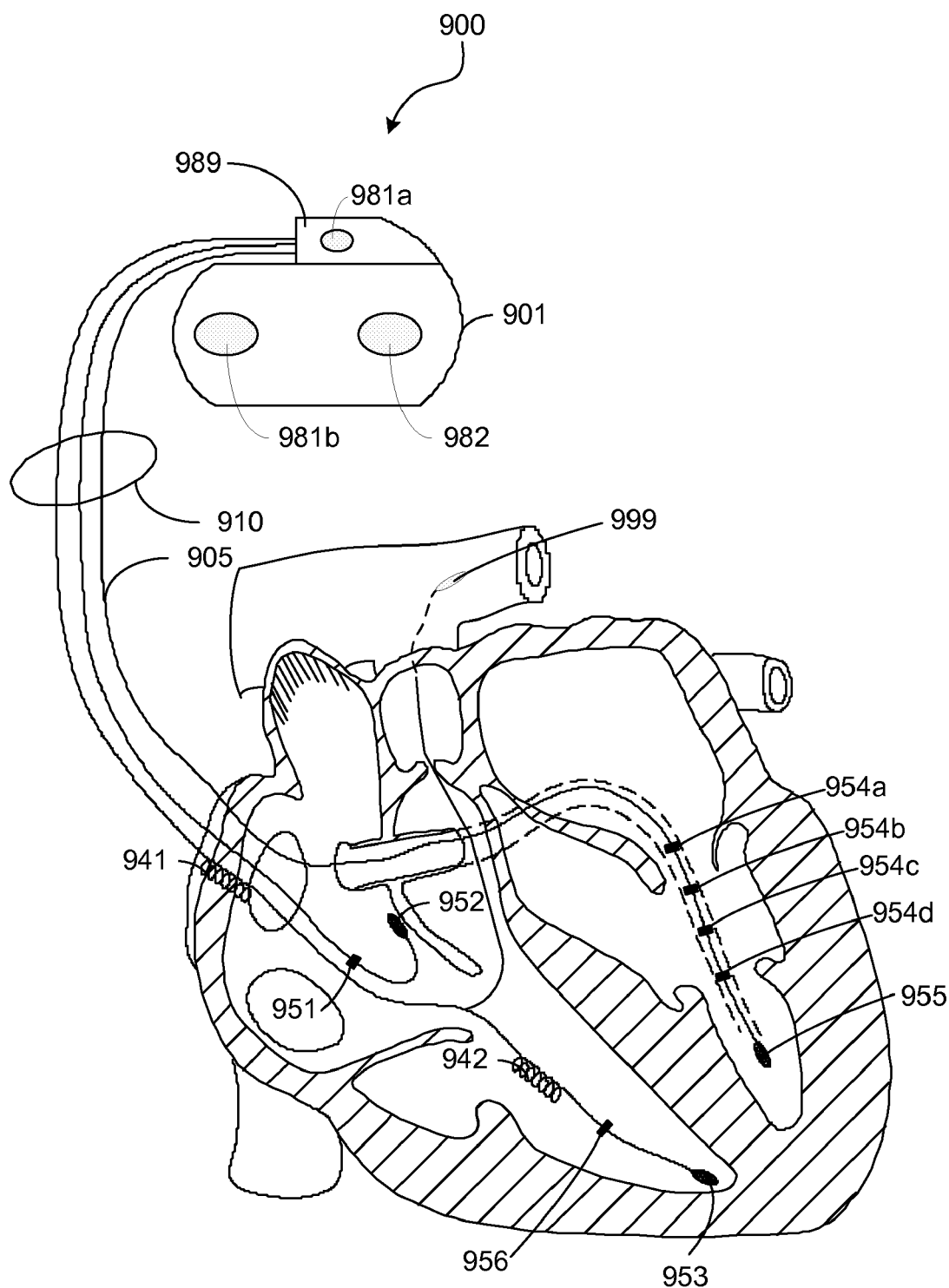
FIG. 9 illustrates a patient-implantable device that may be used in conjunction with a methodology in accordance with embodiments of the present invention.

In reference now to FIG. 9, an embodiment of the present invention is shown implemented through the use of an implanted cardiac therapy device 900. The therapy device 900 includes cardiac rhythm management circuitry enclosed within an implantable housing 901. The CRM circuitry is electrically coupled to an intracardiac lead system 910. Portions of the intracardiac lead system 910 are shown inserted into the patient's heart. The lead system 910 includes cardiac pace/sense electrodes 951-956 positioned in, on, or about one or more heart chambers for sensing electrical signals from the patient's heart and/or delivering pacing pulses to the heart. The intracardiac sense/pace electrodes 951-956 may be used to sense and/or pace one or more chambers of the heart, including the left ventricle, the right ventricle, the left atrium and/or the right atrium. The lead system 910 may include one or more defibrillation electrodes 941, 942 for delivering defibrillation/cardioversion shocks to the heart.

The left ventricular lead 905 incorporates multiple electrodes 954a-954d positioned at various locations within, on or about the left ventricle. Stimulating the ventricle at multiple locations or at a single selected location during a cardiac cycle may provide for increased cardiac output in a patients suffering from HF. In accordance with various embodiments described herein, one or more of the electrodes 954a-954d are selected for pacing the left ventricle. In other embodiments, leads having multiple pacing electrodes positioned at multiple locations within a chamber, such as the one illustrated by the left ventricular lead 905 of FIG. 9, may be implanted within any or all of the heart chambers. A set of electrodes positioned within one or more chambers may be selected. Electrical stimulation pulses may be delivered to the chambers via the selected electrodes according to a timing sequence and output configuration that enhances cardiac function.

Portions of the housing 901 of the implantable device 900 may optionally serve as one or multiple can or indifferent electrodes. The housing 901 is illustrated as incorporating a header 989 that may be configured to facilitate removable attachment between one or more leads and the housing 901. The housing 901 of the therapy device 900 may include one or more can electrodes 981b. The header 989 of the therapy device 900 may include one or more indifferent electrodes 981a.

The housing 901 and/or header 989 may include one or more hemodynamic sensors 982, such as an accelerometer or microphone. One or more cardiac leads 910 or separate sensor leads may incorporate one or more hemodynamic sensors, such as a pulmonary arterial pressure sensor. The cardiac electrodes and/or other sensors disposed within or on the housing 901 or lead system 910 of the therapy device 900 may produce signals used for detection and/or measurement of various physiological parameters, such as transthoracic impedance, respiration rate, minute ventilation, heart rate, cardiac dyssynchrony, activity, posture, blood chemistry, $O_2$ saturation, heart sounds, wall stress, wall strain, hypertrophy, inter-electrode impedance, electrical delays (PR interval, AV interval, QRS width, etc.), activity, cardiac chamber pressure, cardiac output, temperature, heart rate variability, depolarization amplitudes, depolarization timing, and/or other physiological parameters. It is contemplated that, in certain embodiments, information derived from such signals may be incorporated into the optimization algorithm that is employed to provide acute optimization of left ventricular preload in response varying CRT pacing parameters.

In some configurations, the implantable device 900 may incorporate one or more transthoracic impedance sensors that may be used to acquire the patient's respiratory waveform, and/or to acquire other respiratory-related information such as minute ventilation. The transthoracic impedance sensor may include, for example, one or more intracardiac electrodes 941, 942, 951-956 positioned in one or more chambers of the heart. The intracardiac electrodes 941, 942, 951-956 may be coupled to impedance drive/sense circuitry positioned within the housing 901 of the therapy device 900. Information from the transthoracic impedance sensor may be used to adapt the rate of pacing to correspond to the patient's activity or metabolic need, among other uses.

Communications circuitry is disposed within the housing 901 for facilitating communication between the CRM circuitry and a patient-external device, such as an external programmer or advanced patient management (APM) system. The communications circuitry may also facilitate unidirectional or bidirectional communication with one or more implanted, external, cutaneous, or subcutaneous physiologic or non-physiologic sensors, patient-input devices and/or information systems. In certain embodiments, the therapy device 900 may include circuitry for detecting and treating cardiac tachyarrhythmia via defibrillation therapy and/or anti-tachyarrhythmia pacing (ATP). Configurations providing defibrillation capability may make use of defibrillation coils 941, 942 for delivering high energy shocks to the heart to terminate or mitigate tachyarrhythmia.

The implantable therapy device 900 includes a PA pressure sensor 999 disposed in the pulmonary artery and configured to sense pressure therein. The implantable device 900 includes circuitry coupled to the PA pressure sensor for determining RV hemodynamic function based on the sensed signals from the PA pressure sensor 999. As previously described, the device 900 may include circuitry for monitoring RV hemodynamic function during CRT optimization. Additionally or alternatively, the device 900 may include circuitry for determining pacing parameters that provide improved or optimal RV function based on the PA pressure signal.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A cardiac rhythm management system, comprising:
  a cardiac resynchronization optimization module configured to determine pacing parameters for cardiac resynchronization therapy (CRT);
  pacing therapy circuitry configured to deliver pacing using the CRT pacing parameters;
  a pulmonary artery pressure sensor having dimensions to fit within the pulmonary artery and configured to sense pulmonary artery pressure;
  a right ventricular function analysis module configured to analyze the measured pressure to determine right ventricular function achieved during the pacing; and
  a controller configured to generate a signal responsive to a change in the right ventricular function during the pacing, wherein the cardiac resynchronization optimization module comprises a processor configured to implement the right ventricular function analysis module and to generate an alert if the right ventricular function degrades, the processor further configured to allow an override of the selected one or more pacing parameters to achieve an improvement in the right ventricular function.

2. The system of claim 1, further comprising a sensor to determine various patient conditions, wherein the CRT optimization module is configured to select one or more pacing parameters as one or more optimal pacing parameters for the various patient conditions.

3. The system of claim 2, wherein the various patient conditions comprise various patient postures or various patient activity levels.

4. The system of claim 1, wherein the CRT optimization module is configured to determine the pacing parameters based on intrinsic electrical or mechanical events that have a predictable relationship to delivery of optimally timed pacing pulses.

5. The system of claim 1, wherein the right ventricular function analysis module in conjunction with the pulmonary artery pressure sensor and the controller are configured to test the CRT parameters for degradation of right ventricular function by sensing the pulmonary pressure during an acute burst pacing protocol.

6. The system of claim 1, wherein the controller is configured to generate an alert or automatically override the CRT pacing parameters if degradation of the right ventricular function is detected.

7. The system of claim 1, wherein the pacing parameters comprise a pacing timing interval.

8. The system of claim 1, wherein the pacing parameters comprise one or both of an atrioventricular delay interval and an interventricular delay interval.

9. The system of claim 1, wherein the pacing parameters comprise one or more of a pacing site, a pacing mode, and a pacing sequence.

10. The system of claim 1, wherein the pacing parameters are selected to improve left ventricular function under various patient conditions.

11. The system of claim 1, further comprising a sensor configured to measure hemodynamic function of the left ventricle, wherein the cardiac resynchronization optimization module is configured to determine the pacing parameters based on measured left ventricular hemodynamic function.

12. The system of claim 1, wherein the cardiac resynchronization optimization module is configured to determine the pacing parameters based on echocardiographic or electrophysiological studies.

13. The system of claim 1, wherein the pacing therapy circuitry is configured to deliver an acute burst protocol.

14. The system of claim 1, wherein the right ventricular function analysis module is configured to determine one or more of pulmonary artery end diastolic pressure (PAEDP), pulmonary artery end systolic pressure (PAESP), pulmonary artery pulse pressure (PAPP), RV $dp/dt_{max}$, RV $dp/dt_{min}$, and PAEDP timing.

15. The system of claim 1, further comprising a sensor arrangement configured to determine a plurality of patient conditions, wherein the processor is configured to determine the one or more pacing parameters as one or more optimal pacing parameters for the plurality of patient conditions.

16. The system of claim 15, wherein the plurality of patient conditions comprises a plurality of patient postures or a plurality of patient activity levels.

17. The device of claim 15, wherein the processor is further configured to automatically modify the one or more pacing parameters to achieve an improvement in the right ventricular function.

* * * * *